(12) United States Patent
Sugiura et al.

(10) Patent No.: US 10,441,618 B2
(45) Date of Patent: Oct. 15, 2019

(54) MORINGA EXTRACT

(71) Applicants: Kazuhiko Sugiura, Yokkaichi (JP); Aditya Kulkarni, Kawasaki (JP)

(72) Inventors: Kazuhiko Sugiura, Yokkaichi (JP); Aditya Kulkarni, Kawasaki (JP)

(73) Assignee: TAIYO KAGAKU CO., LTD., Yokkaichi-shi (JP)

( * ) Notice: Subject to any disclaimer, the term of this patent is extended or adjusted under 35 U.S.C. 154(b) by 0 days.

(21) Appl. No.: 15/770,620

(22) PCT Filed: Oct. 21, 2016

(86) PCT No.: PCT/JP2016/081237
§ 371 (c)(1),
(2) Date: Apr. 24, 2018

(87) PCT Pub. No.: WO2017/073473
PCT Pub. Date: May 4, 2017

(65) Prior Publication Data
US 2018/0318367 A1    Nov. 8, 2018

(30) Foreign Application Priority Data

Oct. 28, 2015  (JP) ................. 2015-211780
Oct. 28, 2015  (JP) ................. 2015-211781
Dec. 18, 2015  (JP) ................. 2015-247740

(51) Int. Cl.
| A61K 36/18 | (2006.01) |
| A61K 36/185 | (2006.01) |
| A23L 2/52 | (2006.01) |
| A23G 3/34 | (2006.01) |
| A23G 4/00 | (2006.01) |
| A23L 33/105 | (2016.01) |
| A23L 9/10 | (2016.01) |
| A23F 5/46 | (2006.01) |
| A23G 3/48 | (2006.01) |
| A23G 4/06 | (2006.01) |
| A23G 9/42 | (2006.01) |
| A23L 2/54 | (2006.01) |
| A61K 31/7034 | (2006.01) |
| A23G 1/48 | (2006.01) |
| A23G 3/36 | (2006.01) |
| A23L 2/39 | (2006.01) |

(52) U.S. Cl.
CPC ............ *A61K 36/185* (2013.01); *A23F 5/465* (2013.01); *A23G 1/48* (2013.01); *A23G 3/34* (2013.01); *A23G 3/36* (2013.01); *A23G 3/48* (2013.01); *A23G 4/00* (2013.01); *A23G 4/068* (2013.01); *A23G 9/42* (2013.01); *A23L 2/52* (2013.01); *A23L 2/54* (2013.01); *A23L 9/10* (2016.08); *A23L 9/12* (2016.08); *A23L 33/105* (2016.08); *A61K 31/7034* (2013.01); *A23L 2/39* (2013.01); *A23V 2002/00* (2013.01); *A61K 2236/331* (2013.01)

(58) Field of Classification Search
CPC ................................................ A61K 36/185
See application file for complete search history.

(56) References Cited

U.S. PATENT DOCUMENTS

| 2010/0227828 A1 | 9/2010 | Gokaruju et al. |
| 2012/0128607 A1 | 5/2012 | Mandeau et al. |
| 2015/0209395 A1 | 7/2015 | Raskin et al. |

FOREIGN PATENT DOCUMENTS

| JP | 7-304685 A | 11/1995 |
| JP | 4032393 B2 | 1/2008 |
| JP | 2008-237117 A | 10/2008 |
| JP | 4719372 B2 | 7/2011 |
| JP | 2012-530769 A | 12/2012 |
| JP | 2014-208608 A | 11/2014 |
| WO | WO 2013/183065 A2 | 12/2013 |
| WO | WO 2014/053944 A1 | 4/2014 |

OTHER PUBLICATIONS

English translation of the International Search Report (form PCT/ISA/210), dated Jan. 10, 2017, for International Application No. PCT/JP2016/081237, with an English translation.
Gernah et al., "Effect of Boiling Time on the Quality of 'Zogale': A Snack Food Produced from Peanut (*Arachis hypogea*) Cake and Boiled Moringa oleifera Leaves," African Journal of Food Science, vol. 6, No. 10, May 30, 2012, pp. 287-293.
Ikeuchi et al., "Effects of Benzylglucosinolate on Endurance Capacity in Mice," Journal of Health Science, vol. 55, No. 2, 2009 (Published online Jan. 28, 2009), pp. 178-182.

(Continued)

Primary Examiner — Shawquia Jackson
(74) Attorney, Agent, or Firm — Birch, Stewart, Kolasch & Birch, LLP

(57) ABSTRACT

A *moringa* extract containing a benzyl glucosinolate in a content of 6% by mass or more, calculated as a dry solid content of the extract, wherein the extract does not substantially contain an alkaloid. The *moringa* extract of the present invention for solving a first aspect is useful in the field of foodstuff or the like. Also, the PPAR activator of the present invention for solving a second aspect has excellent PPAR activation action, and has no disadvantages in side effects, so that it can be ingested for long term, which can be preferably used in foodstuff and the like. Therefore, the PPAR activator of the present invention for solving a second aspect can be expected to be used as a food, a supplement or a medicament not only for prevention of disease such as insulin resistance, hyperinsulinism, Type 2 diabetes, hypertension, hyperlipidemia, arterial sclerosis and obesity, but also for fatigue recovery or endurance improvement by improving basal metabolism. In addition, a benzyl glucosinolate-containing composition for solving a third aspect is useful in the field of foodstuff or the like.

4 Claims, 1 Drawing Sheet

(56) References Cited

OTHER PUBLICATIONS

Maldini et al., "Moringa oleifera: Study of Phenolics and Glucosinolates by Mass Spectrometry," Journal of Mass Spectrometry, vol. 49, 2014, pp. 900-910.
Michalik et al., "International Union of Pharmacology. LXI. Peroxisome Proliferator-Activated Receptors," Pharmacological Reviews, vol. 58, No. 4, 2006, pp. 726-741.
Orman et al., "Investigating the In-vivo Antiplasmodial Properties of Aqueous Extract of Moringa oleifera Lam (*Moringaceae*) Leaves," British Journal of Pharmaceutical Research, vol. 5, No. 6, Article No. BJPR.2015.040, 2015 (Published Feb. 2, 2015), pp. 419-430.
Sangkitikomol et al., "Effect of Moringa oleifera on Advanced Glycation End-product Formation and Lipid Metabolism Gene Expression in HepG2 Cells," Genetics and Molecular Research, vol. 13, No. 1, 2014, pp. 723-735.
Sohaimy et al., "Biochemical and Functional Properties of Moringa oleifera Leaves and their Potential as a Functional Food," Global Advanced Research Journal of Agricultural Science, vol. 4. No. 4, Apr. 2015, pp. 188-199.
Tanaka, "PPARδ and Metabolic Syndrome," Folia Pharmacologica Japonica, vol. 128, 2006, pp. 225-230.

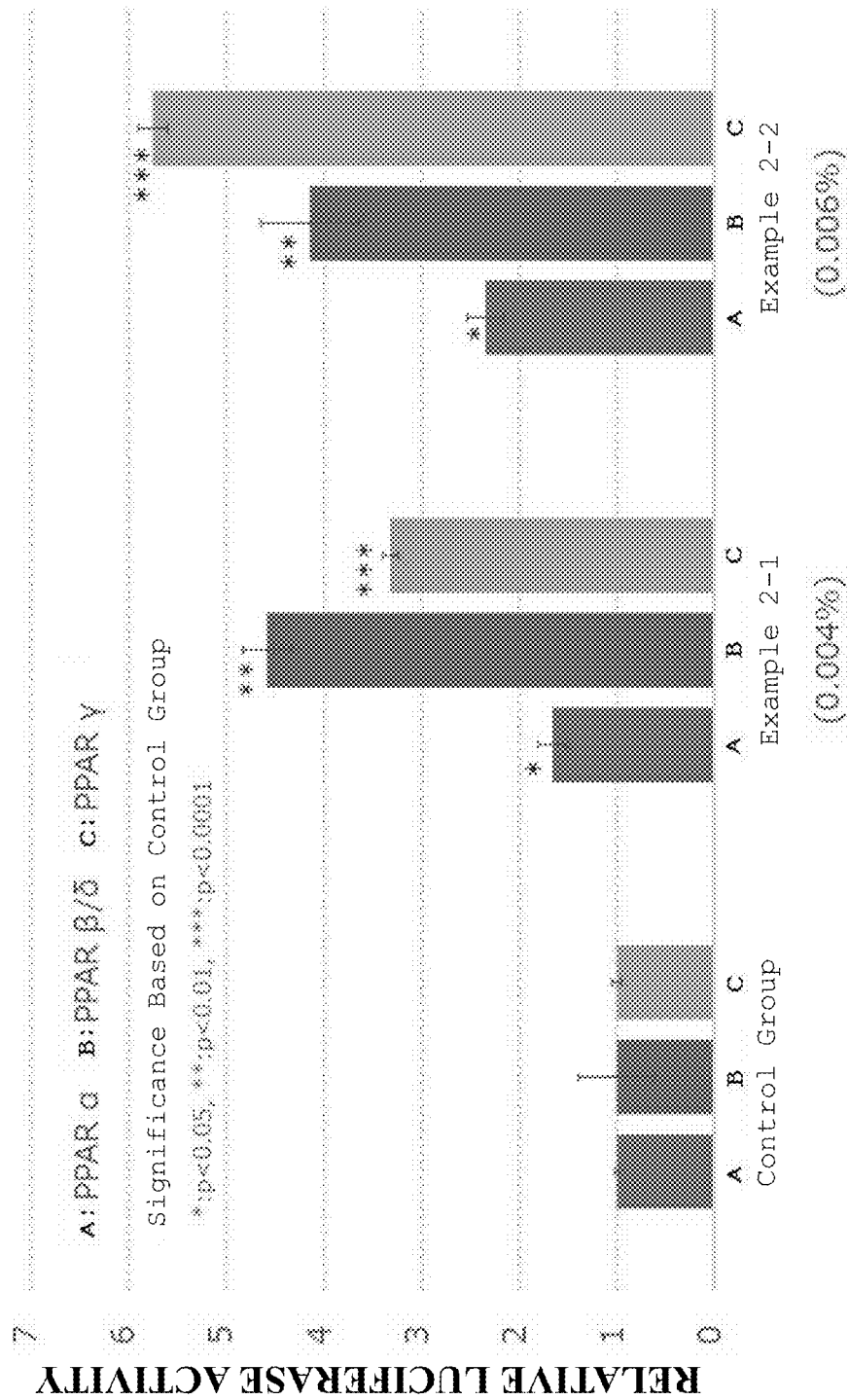

MORINGA EXTRACT

TECHNICAL FIELD

The present invention relates to a *moringa* extract, a PPAR activator containing a *moringa* extract, a composition containing a *moringa* extract, a method for producing them, and foodstuff containing them.

BACKGROUND ART

A plant belonging to the genus *Moringa* (also simply referred to herein to as "*moringa*") is a plant which is widely familiar as a medicinal plant in India, Southeast Asia and the like, and has been found to have various useful physiological functions such as anti-oxidation effects and anti-inflammatory effects. *Moringa* richly contains minerals, amino acids, benzyl glucosinolates (BGLs) and the like as active ingredients for these effects. Recently, a dry pulverized product of leaves or roots of *moringa*, an extract powder which is extracted with hot water, a water-containing alcohol or the like from the pulverized product as a raw material, and the like have been sold as a raw material of a functional food, and are remarked (see, Patent Publications 1 and 2, and Non-Patent Publication 1).

With the improvement in the dietary habits and the development in medicine, global life expectancy is increased. However, patients suffering from lifestyle diseases have been dramatically increased due to insufficiency of exercises or the changes in lifestyles such as changes of eating habits. From such social backgrounds, preventive effects for lifestyle diseases of a food functional component contained in a food which is daily taken are remarked, and in recent years, the institution of Foods with Function Claims has been executed even in Japan. It is important for improving the quality of life by positively ingesting such a food functional component to make an effort in maintaining and promoting health.

Some food functional components are thought to act with a target protein to exhibit their effects in the same manner as a pharmaceutical agent. One of the proteins which are remarked as one of the component is a ligand-dependent transcriptional factor, PPAR (peroxisome proliferator-activated receptor) belonging to an intranuclear receptor superfamily. This PPAR has three subtypes α, β/δ and γ, and the subtypes are involved in lipid metabolism, saccharometabolism and proliferation or differentiation of a cell. It has been reported that the α is mainly expressed in the liver and involved in lipid combustion, that the β/δ is expressed in various tissues mainly including muscles and involved in improvement of physical exercising ability, and that the γ is expressed in a white adipose tissue or a macrophage and involved in inducing differentiation of a fat cell or lipogenesis. Therefore, an activation of PPAR will lead to preventive and ameliorative effects of various diseases such as insulin resistance, diabetes, obesity and hypertension, so that development regarding an activator is expected (Non-Patent Publications 2 and 3).

From the viewpoint mentioned above, a PPAR activator prepared by chemosynthesis of, for example, ibuprofen, leukotrien B4, indomethacin, a fibrate-based compound or the like has been developed as a substance activating a PPAR and known. In addition, as a PPAR activator derived from a natural component, a curcumin contained in a turmeric, a monoacylglycerol which is a member of oils, catechins contained in tea or the like, and the like have been reported (see, Patent Publication 3).

In addition, conventionally, health foods have been utilized for the purpose of supplementing nutrient functions. Among them, a concept with higher needs is a fatigue recovery, and an amino acid such as taurine, or an extract of plants such as a ginseng or a maca has been utilized. Recently, an anti-fatigue effect of a benzyl glucosinolate which is contained in a food derived from Brassicacae including maca has been remarked, and its effects have been confirmed also in an animal experiment. A concentrated product of benzyl glucosinolate or the like is effective to fully exhibit the effects, and it is desired that a concentrated product is provided as a plant extract (see, Patent Publications 4 and 5, and Non-Patent Publication 4).

PRIOR ART REFERENCES

Patent Publications

Patent Publication 1: Japanese Patent No. 4032393
Patent Publication 2: Japanese Patent Laid-Open No. 2008-237117
Patent Publication 3: Japanese Patent No. 4719372
Patent Publication 4: Japanese Patent Laid-Open No. Hei-7-304685
Patent Publication 5: Japanese Unexamined Patent Publication No. 2012-530769

Non-Patent Publications

Non-Patent Publication 1: *Global Advanced Research Journal of Agricultural Science* (ISSN:2315-5094), 4(4), 188-199, April, 2015
Non-Patent Publication 2: *PHARMACOLOGICAL REVIEWS*, 58, 726-741: 2006
Non-Patent Publication 3: *Journal of Pharmacological Sciences*, 128, 225-230:2006
Non-Patent Publication 4: *Journal of Health Science*, 55 (2009), No. 2, 178-182

SUMMARY OF THE INVENTION

Problems to be Solved by the Invention

However, in a *moringa* extract which is an extract of a *moringa*, the content of the extract is lowered by the reason that a part of the above active ingredients is undesirably decomposed in an extraction process of the extract, or the like, so that the useful physiological function is unlikely to be exhibited. Particularly, a benzyl glucosinolate may not likely to be decomposed during extracting the extract, and a further improvement is required.

In addition, plants contain an alkaloid, and also the *moringa* is not an exception. A *moringa* extract obtainable from the *moringa* also contains an alkaloid. It is thought that an oral ingestion of an ordinary amount of a *moringa* by ordinary person is safe, but if pregnant women take a *moringa*, there is a risk of uterine contraction or miscarriage. Accordingly, a further improvement is desired for the safety of a *moringa* extract.

Therefore, a first aspect of the present invention is to provide a *moringa* extract having useful physiological function and high safety.

In addition, in a case of a synthetic material, there is a disadvantage of side effects due to long term ingestion, so that the *moringa* extract is not suitable for the continuous ingestion in daily life. Additionally, even if a *moringa* extract is derived from a natural component, a PPAR activator derived from a natural component which has been so far reported is not said to be sufficient in an activation effect.

Therefore, a second aspect of the present invention is to provide a PPAR activator derived from a natural component excellent in an activation of the PPAR.

In addition, it is difficult to prepare an extract which is stable in the quality by the reason that a benzyl glucosinolate is likely to be decomposed when produced from a plant extract, or the like. It is confirmed that a benzyl glucosinolate is contained in not only Brassicacae but also a *moringa* which is Moringaceae; however, the same applies to the benzyl glucosinolate of a *moringa*, and it is difficult to provide in a stable state in quality because it is likely to be decomposed during the production or the like.

Therefore, a third aspect of the present invention is to provide a benzyl glucosinolate-containing composition which inhibits the decomposition of a benzyl glucosinolate and is excellent in stability.

Means to Solve the Problems

When the above first aspect is studied, the present inventors have found that the content of the benzyl glucosinolate can be increased, and a *moringa* extract not substantially containing an alkaloid in the *moringa* extract can be obtained by carrying out the extraction under particular conditions. The present inventors have intensively studied based on such findings, and the present invention has been perfected thereby.

The present invention for solving the first aspect relates to the following [1] to [3]:

[1] a *moringa* extract containing a benzyl glucosinolate in a content of 6% by mass or more, calculated as a dry solid content of the extract, wherein the extract does not substantially comprise an alkaloid;

[2] a method for producing a *moringa* extract, including extracting a *moringa* pre-treated at 80° C. or higher with a solvent at a temperature of from 10° to 50° C.; and

[3] foodstuff containing a *moringa* extract as defined in [1].

The present invention for solving the second aspect relates to the following [1] to [3]:

[1] a peroxisome proliferator-activated receptor (PPAR) activator containing a *moringa* extract;

[2] foodstuff containing a PPAR activator as defined in [1]; and

[3] a method for producing a PPAR activator containing a *moringa* extract, including extracting a *moringa* pre-treated at 80° C. or higher with a solvent at a temperature of from 10° to 50° C.

When the third aspect is studied, the present inventors have found that the decomposition of a benzyl glucosinolate can be inhibited by mixing a *moringa* extract which is an extract or a *moringa* with an excipient under particular conditions. The present inventors have made intensive studies based on such findings, thereby perfecting the present invention.

The present invention for solving the third aspect relates to the following [1] to [3]:

[1] a benzyl glucosinolate-containing composition containing a *moringa* extract and an excipient, wherein the content of the above excipient is 65 parts by mass or more based on 100 parts by mass of a dry solid content of the *moringa* extract;

[2] foodstuff containing a composition as defined in [1]; and

[3] a method for producing a benzyl glucosinolate-containing composition, including mixing a *moringa* extract with an excipient, wherein a blending amount of the above excipient is from 65 to 1,000 parts by mass based on 100 parts by mass of a dry solid content of the above *moringa* extract.

Effects of the Invention

According to the present invention for solving the first aspect, a *moringa* extract having a useful physiological function and high safety can be provided.

According to the present invention for solving the second aspect, a PPAR activator derived from natural component which is excellent in an activation of PPAR can be provided.

According to the present invention for solving the third aspect, a benzyl glucosinolate-containing composition which inhibits the decomposition of a benzyl glucosinolate and is excellent in safety can be provided.

BRIEF DESCRIPTION OF THE DRAWINGS

FIG. 1 is a graph showing relative luciferase activity.

MODES FOR CARRYING OUT THE INVENTION

An embodiment of the present invention for solving the first aspect will be explained hereinbelow.

A *moringa* extract of this embodiment contains a benzyl glucosinolate. It is known that the benzyl glucosinolate has a useful physiological function such as anti-fatigue, anti-oxidation, nutrition enhancement and hormone control. The *moringa* extract of this embodiment contains a benzyl glucosinolate in a given amount or more, thereby exhibiting these functions. Incidentally, the fatigue includes fatigues caused by environmental factors such as simple exercises, social activity, temperature or humidity, which are indicated as symptoms such as slowness in movement, decrease in exercising amount, scattered attention, lowered stimuli-responsiveness or the like, and skin fatigues such as flabbiness, wrinkles of skin or the like. The fatigue in the anti-fatigue as referred to in this embodiment includes both the fatigues, and the anti-fatigue is preferably against the former fatigues. When DPPH radical scavenging activity of the *moringa* extract of this embodiment is measured in accordance with a method described in the section of Examples set forth below, IC50 value is preferably 600 μg/ml or less, more preferably 300 μg/ml or less, and even more preferably 100 μg/ml or less.

The content of the benzyl glucosinolate in the *moringa* extract, calculated as a dry solid content of the extract, is 6% by mass or more, preferably 10% by mass or more, and more preferably 15% by mass or more, and the upper limit can be, but not particularly limited to, for example, 50% by mass or less, from the viewpoint of exhibiting useful physiological functions.

The content of the benzyl glucosinolate in the *moringa* extract as used herein refers to an amount analyzed in accordance with a method of Zhang et al. (Referential Publication: Zhang, Y., Wade, K, L., Prestera, T., and Talalay, P. Anal. Biochem. 239: 160-167, 1996). Specifically, the method is a method including treating a *moringa* extract with a myrosinase, and analyzing and quantifying a reaction product (1,3-benzenedithiol-2-thione) formed when a treated product is reacted with 1,2-benzenedithiol in a weakly alkaline buffered solution with a reverse phase high-performance liquid chromatography (detection: UV 365 nm).

The *moringa* extract of this embodiment does not substantially contain an alkaloid, and preferably does not contain an alkaloid at all. As to the phrase not substantially containing an alkaloid as used herein, in a case where a dry powder of the *moringa* extract is made as a sample, 100 mg of the samples are dissolved in 100 mL of methanol, 100 μL of the solutions are dropped onto a thin layer plate (at that time, an amount of the dropped sample is about 100 micrograms), the droplet is developed with a developing solvent, thereafter Dragendorff reagent is sprayed, and the plate is not colored, it is judged as not substantially containing. Here, the detection limit of an alkaloid at that time is 1 microgram, and the detection limit in the sample is about 1%.

Thin Layer Chromatography Analytical Conditions

The measurements are carried out using Silica Gel 60F manufactured by Merck as a thin layer plate, chloroform/methanol/25% aqueous ammonia (75/25/2, v/v/v) as a developing solvent, and Dragendorff reagent as a coloring reagent, respectively.

The alkaloid to be detected includes spirochin and the like.

The *moringa* extract of this embodiment can contain free amino acids, and can further contain one or more amino acids selected from the group consisting of, for example, arginine, glutamic acid, alanine, methionine and cysteine.

The content of the free amino acids in the *moringa* extract is preferably 0.1% by mass or more calculated as a dry solid content of the extract, and more preferably 0.5% by mass or more, and the upper limit can be, but not particularly limited to, for example, 2.0% by mass or less, from the viewpoint of health enhancement. When the free amino acids are contained in two or more kinds, the content refers to the total amount.

The *moringa* extract of this embodiment is obtained by extraction from a *moringa* with a solvent.

The *moringa* to be extracted includes, but not particularly limited to, for example, *Moringa oleifera, Moringa concanensis, Moringa drouhardii* or the like. Among them, *Moringa oleifera* is preferred, from the viewpoint that the *Moringa oleifera* is widely cultivated and can be easily harvested. *Moringa oleifera* is a deciduous small arbor which is grown in India in origin, and has other names such as Horseradish tree, Ben nut, *Malungai* (in Tagalog), *Sanjanaa* (in Hindu) and the like.

As a part of a *moringa* to be extracted, all of stems, leaves, sheaths (fruit flesh) and seeds can be used. These parts may be used in the raw, or may be used after drying, and it is preferable that these parts are used after dry, from the viewpoint of the storage stability as a raw material and an yield during the production of an extract. In addition, it is preferable that the fruit flesh or seeds are used, and more preferably seeds are used, from the viewpoint of parts containing an alkaloid in a relatively small amount, in view of the amount distributed according to the parts of the alkaloid. When the seeds are used, the seeds may be used after removal of the exodermis of the seeds, or may be used after pulverization into a powder. It is preferable that the powdered product obtained by pulverizing the seeds with exodermis is used, from the viewpoint of easily producing an extract. On the other hand, even in a case of the parts such as leaves or stems in which the amount of an alkaloid is large, a *moringa* extract not substantially containing an alkaloid can be obtained in accordance with a production method of an embodiment described later. The production method of the embodiment described later has the technical significance even from this point.

In addition, the *moringa* extract is pre-treated before extraction, from the viewpoint of increasing the content of a benzyl glucosinolate in the *moringa* extract obtained. One embodiment of the pretreatment includes a treatment including treating the above mentioned dry powder of the *moringa* or the like at a temperature of 80° C. or higher, and preferably from 80° to 170° C., for example, in a solution at a temperature of preferably from 80° to 95° C., and more preferably from 85° to 90° C. for 1 to 10 minutes, and more preferably 3 to 5 minutes. In this embodiment, the pretreatment for a relatively short time period is effective, but when the treatment is carried out exceeding 10 minutes the benzyl glucosinolate is undesirably decomposed due to its poor thermal stability. In addition, the pretreatment of within 10 minutes is preferred, from the viewpoint of inhibition of alkaloid extraction.

The pretreatment of this embodiment includes, but not particularly limited to, hot water boiling, oil frying, roasting, and the like. When a solvent is used, the solvent includes water, ethanol, an animal or plant fat or oil, or a mixture thereof, and water is preferred, from the viewpoint of safety.

It is assumed that by the pretreatment described above, a protein which is considered to be a decomposition-promoting component of a benzyl glucosinolate can be degenerated, and a decomposition-promoting activity can be inactivated, thereby increasing the content of the benzyl glucosinolate in the *moringa* extract. Incidentally, a hot water extraction has been conventionally carried out, but a long time extraction exceeding 10 minutes is required for a sufficient extraction of the extract. Therefore, the conventional methods have some disadvantages such as decomposition of the benzyl glucosinolate due to heat or extraction of an alkaloid in a large amount, as mentioned above. On the other hand, in the pretreatment of this embodiment, a low temperature extraction described later is carried out after the pretreatment of within 10 minutes, so that it is assumed that the activity of the above protein can be inactivated without causing the disadvantages.

A protein which is considered to be a decomposition-promoting component of a benzyl glucosinolate includes a myrosinase and the like.

The pretreatment is not limited in this embodiment, and embodiments of the known treatment for inactivating these proteins can be taken.

As the solvent used in the extraction, water or an organic solvent containing water is used. The organic solvent includes lower alcohols which can be mixed with water (a monohydric or polyhydric alcohol containing 1 to 4 carbon atoms such as methanol, ethanol, propanol, propylene glycol, butylene glycol, and glycerol), acetone and the like. These organic solvents may be previously mixed with water and used, or two or more kinds of the organic solvents may be mixed with water and used. Extraction only with water is preferred, from the viewpoint of safety.

The liquid amount of the solvent used in the extraction is, but not particularly limited to, for example, from 200 to 3,000 parts by mass, based on 100 parts by mass of the *moringa* to be extracted.

The temperature of the solvent at the time of extraction is from 10° to 50° C., and preferably from 20° to 40° C., from the viewpoint of production efficiency and the lowering of the content of the alkaloid in the *moringa* extract. In accordance with a high temperature extraction at a temperature which exceeds 50° C. that is conventionally known, an alkaloid would be contained in the *moringa* extract obtained in a considerable amount, but it has been found that the extraction at a lower temperature surprisingly lowers the content of the alkaloid. The mechanism in which the content of the alkaloid is lowered is not clarified, but it is assumed that the low-temperature conditions inhibit the extraction of the alkaloid.

The extraction time can be, but not particularly limited to, for example, from 30 to 150 minutes, from the viewpoint of production efficiency.

The extraction can be carried out in a state with stirring or a static state. In addition, when the pretreatment is carried out with a solvent used in the extraction, the pretreatment and the extraction can be continuously carried out. For example, an embodiment of treating a *moringa* at 80° C. or higher for 1 to 10 minutes, thereafter temperature-controlling to 10° to 50° C., and extracting an extract, and the like is included.

After the extraction, the mixture is subjected to a treatment such as filtration or centrifugation to remove the residues, and thereafter an extraction solvent can be removed by subjecting the treated product to a reduced pressure or the like. In addition, the extract can be optionally dried with a spray-drier or the like in a case where an extract is formed into a powder, and the like.

Since the *moringa* extract of this embodiment thus obtained richly contains benzyl glucosinolates, the *moringa* extract can exhibit useful physiological functions. In addition, since the *moringa* extract of this embodiment does not substantially contain an alkaloid, the extract has no problem in a case where pregnant women take the extract, and has high safety.

The *moringa* extract of this embodiment may be either a liquid or a solid, and a solid state such as powder is preferred, from the viewpoint of easiness in transport.

In a case of powder, the extract may be directly circulated in the market as a manufactured product, or may be blended with an excipient to prepare a *moringa* extract-containing composition. A *moringa* extract-containing composition containing the *moringa* extract and an excipient is preferred, from the viewpoint of preventing the solidification of the *moringa* extract and from the viewpoint of inhibiting the decomposition of benzyl glucosinolate to make the quality stable. A method of blending an excipient to the *moringa* extract is preferred as a method of stabilizing the *moringa* extract, as mentioned above.

The excipient includes lactose, starch, cyclodextrin, galactomannan, dextrin, maltodextrin or the like, preferably cyclodextrin, dextrin or maltodextrin, and more preferably dextrin or maltodextrin, from the viewpoint of accomplishment of use or allergen property.

The content of the excipient in the *moringa* extract-containing composition of this embodiment, based on 100 parts by mass of a dry solid content of the *moringa* extract, is, but not particularly limited to, preferably 65 parts by mass or more, and more preferably 100 parts by mass or more, from the viewpoint of stability, and the content is preferably 1,000 parts by mass or less, and more preferably 500 parts by mass or less, from the viewpoint of lowering the excipient used to lower the costs.

The timing of addition of the excipient is not particularly limited, and examples of the timing include during the extraction, after removal of the insoluble residues during the production of the extract, before formation into a powder, and the like, and the addition is carried out preferably after removal of the insoluble residues or before formation into a powder, and more preferably after removal of the insoluble residues, from the viewpoint of improving filtrability.

The *moringa* extract of this embodiment can be blended to various foodstuff. For example, the foodstuff may be refreshing beverages, carbonated beverages, nutrition beverages, fruit beverages, beverages such as lactic acid beverages, concentrated stock solutions or powders for preparing these beverages, or the like.

In addition, this *moringa* extract can be added to a cold confectionery such as ice cream, sherbet, and frappe (kaki kori), noodles such as buckwheat noodles (soba), wheat noodles (udon), fen-tiao, skin of dumplings stuffed with minced pork, skin of shao-mai, Chinese noodles or instant noodles. Further, this *moringa* extract can also be added to a confectionery such as a candy, a chewing gum, a chocolate, a tablet candy, a gummy candy, a snack, a biscuit, a jerry, a custard pudding, a jam, a cream, or a baked confectionery.

Also, the *moringa* extract can be added to a marine or livestock processed food such as tubular roll of steamed fish paste, ham, or sausage, or a dairy product such as a processed milk or a fermented milk, or can be added to a fat or oil and a fat or oil processed food such as salad oil, tempura oil, margarine, mayonnaise, shortening, whipped cream, and salad dressing, or can be added to a seasoning such as a sauce or a gravy sauce, or to a soup, a stew, a salad, a ready-made side dish, or a pickle. In addition, the *moringa* can be added and used in various forms of health and nutritional supplemental foods such as tablets, capsules and drinks, and other quasi-drugs such as oral cavity refreshing agents that are used in the oral cavity such as oral refreshing agent and oral deodorizing agents, dentifrices, and mouthwashes, emollient creams, emollient lotions, or the like.

The blending amount of the *moringa* extract of this embodiment is not particularly limited, and the *moringa* extract can be blended to foodstuff so as to have the concentration of, for example, from 0.01 to 80% by mass calculated as a dry solid content of the extract. Therefore, the content of the benzyl glucosinolate can be from 0.0006 to 40.0% by mass of the foodstuff of this embodiment. In addition, the foodstuff of this embodiment do not substantially contain an alkaloid derived from the blended *moringa* extract.

The foodstuff containing the *moringa* extract of this embodiment richly contain a benzyl glucosinolate, so that the foodstuff can exhibit useful physiological functions. In addition, the foodstuff containing the *moringa* extract of this embodiment do not substantially contain an alkaloid derived from the blended *moringa* extract, so that the foodstuff have high safety as compared to foodstuff blended with the conventional *moringa* extract.

An embodiment of the present invention for solving the second aspect will be explained hereinbelow.

As a result of conducting a series of studies on a PPAR activator derived from a natural component in order to solve the above second aspect, the present inventor has found that the extract extracted from a *moringa* has an excellent PPAR activation action, and the present invention has been accomplished thereby. The *moringa* has been eaten for a long time mainly in India or Southeast Asia regions, and safety thereof has been confirmed, so that the *moringa* can be added to foods and the like and conventionally taken for a long time because the *moringa* does not impair tastes distinctively owned by the foods even when added to the foods and the like.

The PPAR activator of this embodiment contains a *moringa* extract. As the *moringa* extract, a commercially available *moringa* extract may be used, or an extract may be extracted from any parts of the above *moringa* with a solvent. Here, when the extract extracted from any parts of the *moringa* is used, it is preferred that an extract extracted from seeds of *moringa* (also referred to as "extract of seeds")

is used, from the viewpoint of a PPAR activation action. A method for extracting an extract from seeds of *moringa* includes, for example, the following embodiments.

The *moringa* to be extracted includes, but not particularly limited to, for example, *Moringa oleifera, Moringa concanensis, Moringa drouhardii* or the like. Among them, *Moringa oleifera* is preferred from the viewpoint that the *Moringa oleifera* is widely cultivated and can be easily harvested. *Moringa oleifera* is a deciduous small arbor which is grown in India in origin, and has other names such as Horseradish tree, Ben nut, *Malungai* (in Tagalog), *Sanjanaa* (in Hindu) and the like.

The seeds of the *moringa* to be extracted may be used in the raw or may be used after drying, and it is preferred that the seeds are used after drying, from the viewpoint of storage stability as a raw material or an yield during the production of the extract. The seeds may be used after removal of the exodermis of the seeds, or may be used after pulverization into a powder, and it is preferred that the powdered product obtained by pulverizing the seeds with exodermis is used, from the viewpoint of easily producing an extract.

The seeds of the *moringa* to be extracted can be optionally pre-treated before extraction, in order to increase the content of a functional component such as benzyl glucosinolate in the seed extract. It is preferable that the seed extract richly containing a functional component such as a benzyl glucosinolate is used as a PPAR activator, from the viewpoint of giving various useful physiological functions such as anti-oxidation effects or anti-inflammatory effects to the PPAR activator. This pretreatment is a treatment for degenerating or inactivating components which promotes decomposition of a benzyl glucosinolate or the like during or after extracting the extract. Embodiments of this pretreatment include the above dry powder of the *moringa* seeds or the like, and one embodiment of the pretreatment includes a method of treating the above dry powder of the *moringa* or the like at a temperature of 80° C. or higher, and preferably from 80° to 170° C., for example, in a liquid at a temperature of preferably from 80° to 95° C., and more preferably from 85° to 90° C. for 1 to 10 minutes, and more preferably 3 to 5 minutes. In addition, the pretreatment of this embodiment includes, but not particularly limited to, hot water boiling, oil frying, roasting, and the like. When a solvent is used, the solvent includes water, ethanol, an animal or plant fat or oil, or a mixture thereof, and water is preferred, from the viewpoint of safety.

As the solvent used in the extraction, water or an organic solvent containing water can be used. This organic solvent includes lower alcohols which can be mixed with water (a monohydric or polyhydric alcohol containing 1 to 4 carbon atoms such as methanol, ethanol, propanol, propylene glycol, butylene glycol, and glycerol), acetone and the like. These organic solvents may be previously mixed with water and used, or two or more kinds of the organic solvents may be mixed with water and used. Extraction only with water is preferred, from the viewpoint of safety.

The liquid amount of the solvent used in the extraction can be, but not particularly limited to, for example, from 200 to 3,000 parts by mass, based on 100 parts by mass of the *moringa* seeds to be extracted.

The temperature of the solvent at the time of extraction can be, but not particularly limited to, for example, from 10° to 95° C. The extraction at a relatively low temperature is preferred, for example, at a temperature of preferably from 10° to 50° C., and more preferably from 20° to 40° C., from the viewpoint of lowering the content of an alkaloid in the seed extract. The alkaloid includes spirochin and the like. By using a seed extract in which the content of the alkaloid is lowered as a PPAR activator, it is possible to safely ingest the PPAR activator for a longer term, and is preferred. Specifically, a PPAR activator not substantially containing an alkaloid derived from the seed extract or not containing an alkaloid at all is preferred.

The extraction time can be, but not particularly limited to, for example, from 30 to 150 minutes, from the viewpoint of production efficiency.

The extraction can be carried out in a state with stirring or a static state. In addition, when the pretreatment is carried out with a solvent used in the extraction, the pretreatment and the extraction can be continuously carried out. For example, an embodiment of treating a *moringa* at 80° C. or higher for 1 to 10 minutes, thereafter temperature-controlling a treated product to 10° to 50° C., and extracting an extract, and the like is included.

After the extraction, the mixture is subjected to a treatment of filtration, centrifugation, or the like to remove the residues, and thereafter an extraction solvent is removed by applying a reduced pressure or the like, whereby a seed extract can be obtained. In addition, the seed extract can be optionally dried with a freeze-drier, a spray-drier or the like in a case where the seed extract is formed into a powder or the like. The seed extract may be either a liquid or a solid, and a solid state such as powder is preferred, from the viewpoint of easiness in transport.

The content of the *moringa* extract in the PPAR activator can be, but not particularly limited to, for example, from 5 to 100% by mass.

The PPAR activator can contain optional additives such as an excipient or a lubricant.

The excipient includes lactose, starch, cyclodextrin, galactomannan, dextrin, maltodextrin, or the like, and preferably cyclodextrin, dextrin, or maltodextrin, and more preferably dextrin or maltodextrin from the viewpoint of accomplishment of use or allergen property.

The content of the excipient in the PPAR activator, based on 100 parts by mass of a dry solid content of the *moringa* extract, is, but not particularly limited to, preferably 65 parts by mass or more, and more preferably 100 parts by mass or more, from the viewpoint of safety, and the content is preferably 1,000 parts by mass or less, and more preferably 500 parts by mass or less, from the viewpoint of reducing the excipient used to lower the costs.

The timing of the addition of the excipient is not particularly limited, and the timing includes during extraction of the *moringa* extract, after removal of the insoluble residues during production of the extract, before formation into a powder, and the like. The addition is carried out preferably after removal of the insoluble residues or before formation into a powder, and more preferably after removal of the insoluble residues, from the viewpoint of improving filtrability.

In the PPAR activator of this embodiment, a PPAR to be activated may be any one of three subtypes, $\alpha$, $\beta/\delta$ and $\gamma$, and PPAR $\beta/\delta$ is preferred, and it is more preferred that all the subtypes are activated. By the activation, the PPAR activator regulates or induces a fatty acid metabolism such as uptake of a fatty acid in, for example, skeletal muscles, the brain, the liver, heart muscles, the small intestine, the spleen, or the adipose tissues, and a transport, and oxidation and uncoupling protein.

Incidentally, the subject of this embodiment is effective in a mammal having PPAR, including human, mice, rats, rabbits, dogs, cats, cows, horses, pigs, monkeys, and the like.

The PPAR activator of this embodiment can be blended to various foodstuff for one or more purposes selected from the group consisting of, for example, recovery of physical and asthenopic fatigues, improvement of systemic and muscular endurance, prevention and amelioration of hypertension, prevention and amelioration of hyperlipidemia, prevention and amelioration of obesity, prevention and amelioration of diabetes, and prevention and amelioration of insulin resistance and hyperinsulinism.

The foodstuff include, for example, beverages such as refreshing beverages, carbonated beverages, nutrition beverages, fruit beverages, lactic acid beverages; concentrated original liquids or powders for preparing these beverages; cold confectioneries such as ice cream, sherbet, and frappe (kaki kori); noodles such as buckwheat noodles (soba), wheat noodles (udon), fen-tiao, skin of dumplings stuffed with minced pork, skin of shao-mai, Chinese noodles or instant noodles; confectioneries such as a candy, a chewing gum, a chocolate, a tablet candy, a gummy candy, a snack, a biscuit, a jerry, a custard pudding, a jam, a cream, or a baked confectionery; a marine or livestock processed food such as tubular roll of steamed fish paste, ham, or sausage; a dairy product such as a processed milk or a fermented milk; a fat or oil and a fat or oil processed food such as salad oil, tempura oil, margarine, mayonnaise, shortening, whipped cream, and salad dressing; a seasoning such as a sauce or a gravy sauce; a soup, a stew, a salad, a ready-made side dish, a pickle or the like; various forms of health and nutritional supplemental foods in the forms of tablets, capsules, finely pulverized agents (including powders), liquid (including syrups); supplements; and drinks, and other oral cavity refreshing agents that are used in the oral cavity such as oral refreshing agents and oral deodorizing agents; foodstuff for a pet, or the like.

The blending amount of the PPAR activator is not particularly limited, and the PPAR activator can be blended so as to have a concentration, for example, from 0.0001 to 80% by mass calculated as a dry solid content of the extract.

An embodiment of the present invention for solving the third aspect will be explained hereinbelow.

The benzyl glucosinolate-containing composition of this embodiment contains a *moringa* extract and an excipient. By including the excipient, a mechanism capable of inhibiting the decomposition of a benzyl glucosinolate in the *moringa* extract is not certain, but it is assumed that hydrolysis of benzyl glucosinolate is delayed by the excipient.

The *moringa* extract contained in the composition of this embodiment contains a benzyl glucosinolate. The content of the benzyl glucosinolate in the *moringa* extract is preferably 6% by mass or more, more preferably 10% by mass or more, and even more preferably 15% by mass or more, calculated as a dry solid content of the extract, from the viewpoint of exhibiting useful physiological functions, and the upper limit can be, but not particularly limited to, for example, 50% by mass or less.

A *moringa* extract not substantially containing an alkaloid is preferred, and a *moringa* extract not containing alkaloid at all is more preferred.

The *moringa* extract can contain free amino acids, and further can contain one or more amino acids selected from the group consisting of, for example, arginine, glutamic acid, alanine, methionine, and cysteine.

The content of the free amino acids in the *moringa* extract is preferably 0.1% by mass or more, and more preferably 0.5% by mass or more calculated as a dry solid content of the extract, from the viewpoint of enhancing health, and the upper limit can be, but not particularly limited to, for example, 2.0% by mass or less. When two or more kinds of the free amino acids are contained, the content of the free amino acids refers to the total content.

The *moringa* extract may be extracted from a *moringa* with a solvent or a commercially available extract may be used. A commercially available extract includes, for example, *Moringa* Extract 5% (manufactured by Apollo Ingredient, India) and the like. Some embodiments including extracting from a *moringa* will be explained hereinbelow.

The *moringa* to be extracted includes, but not particularly limited to, for example, *Moringa oleifera, Moringa concanensis, Moringa drouhardii* or the like. Among them, *Moringa oleifera* is preferred, from the viewpoint that the *Moringa oleifera* is widely cultivated and can be easily harvested. *Moringa oleifera* is a deciduous small arbor which is grown in India in origin, and has other names such as Horseradish tree, Ben nut, *Malungai* (in Tagalog), *Sanjanaa* (in Hindu) and the like.

As a part of a *moringa* to be extracted, all of stems, leaves, sheaths (fruit flesh) and seeds can be used. These parts may be used in the raw, or may be used after drying, and it is preferable that these parts are used after drying, from the viewpoint of the storage stability as a raw material and an yield during the production of an extract. In addition, it is preferable that the fruit flesh or seeds are used, and more preferably seeds are used, from the viewpoint of parts containing an alkaloid in a relatively small amount, in view of the amount distributed according to the parts of the alkaloid. When the seeds are used, the seeds may be used after removal of the exodermis of the seeds, or may be used after pulverization into a powder. It is preferable that the powdered product obtainable by pulverizing the seeds with exodermis is used, from the viewpoint of easily producing an extract. On the other hand, even in the parts of leaves, stems, or the like that richly contain an alkaloid, a *moringa* extract not substantially containing an alkaloid can be obtained in accordance with a production method of an embodiment described later.

In addition, it is preferable that the *moringa* extract is optionally pre-treated before extraction, from the viewpoint of increasing the content of a benzyl glucosinolate in the *moringa* extract obtained. One embodiment of the pretreatment includes a method including treating the above dry powder of the *moringa* or the like at a temperature of 80° C. or higher, and preferably from 80° to 170° C., for example, in a solution at a temperature of preferably from 80° to 95° C., and more preferably from 85° to 90° C. for 1 to 10 minutes, and more preferably 3 to 5 minutes. In this embodiment, the pretreatment for a relatively short time period is effective. In addition, the pretreatment of within 10 minutes is preferred, from the viewpoint of inhibition of alkaloid extraction.

The pretreatment of this embodiment includes, but not particularly limited to, hot water boiling, oil frying, roasting, and the like. When a solvent is used, the solvent includes water, ethanol, an animal or plant fat or oil, or a mixture thereof, and water is preferred, from the viewpoint of safety.

As the solvent used in the extraction, water or an organic solvent containing water is used. This organic solvent includes lower alcohols which can be mixed with water (a monohydric or polyhydric alcohol containing 1 to 4 carbon atoms such as methanol, ethanol, propanol, propylene glycol, butylene glycol, and glycerol), acetone and the like. These organic solvents may be previously mixed with water and used, or two or more kinds of the organic solvents may be mixed with water and used. Extraction only with water is preferred from the viewpoint of safety.

The liquid amount of the solvent used in the extraction can be, but not particularly limited to, for example, from 200 to 3,000 parts by mass, based on 100 parts by mass of the *moringa* to be extracted.

The temperature of the solvent at the time of extraction can be, but not particularly limited to, for example, from 10° to 95° C., and the temperature is, for example, preferably from 10° to 50° C., and more preferably from 20° to 40° C., from the viewpoint of production efficiency and the lowering of the content of an alkaloid in the *moringa* extract.

The extraction time can be, but not particularly limited to, for example, from 30 to 150 minutes, from the viewpoint of production efficiency.

The extraction can be carried out in a state with stirring or a static state. In addition, when the pretreatment is carried out with a solvent used in the extraction, the pretreatment and the extraction can be continuously carried out. For example, an embodiment of treating a *moringa* at 80° C. or higher for 1 to 10 minutes, thereafter temperature-controlling to 10° to 50° C., and extracting an extract, and the like is included.

After the extraction, the mixture is subjected to a treatment such as filtration or centrifugation to remove the residues, and thereafter an extraction solvent can be removed by applying a reduced pressure or the like. In addition, the seed extract can be optionally dried with a spray-drier or the like in a case where an extract is formed into a powder or the like.

The *moringa* extract at the time of the extraction may be either a liquid or a solid, and a solid state such as powder is preferred as a *moringa* extract usable in the composition of this embodiment.

An excipient contained in the benzyl glucosinolate-containing composition of this embodiment can contain, for example, one or more members selected from the group consisting of maltodextrin, galactomannan, cyclodextrin, dextrin, starch, and lactose, preferably one or more members selected from the group consisting of maltodextrin, galactomannan, and cyclodextrin, and more preferably maltodextrin, from the viewpoint of accomplishment of use or allergen property.

The content of the excipient in the benzyl glucosinolate-containing composition of this embodiment, based on 100 parts by mass of the dry solid content of the *moringa* extract in the benzyl glucosinolate-containing composition, is 65 parts by mass or more, and preferably 100 parts by mass or more, from the viewpoint of safety, and the content is preferably 1,000 parts by mass or less, and more preferably 500 parts by mass or less, from the viewpoint of reducing the excipient used to lower the costs. Therefore, the content of the excipient of this embodiment includes preferred ranges of from 65 to 1,000 parts by mass, from 65 to 500 parts by mass, from 65 to 100 parts by mass, from 100 to 1,000 parts by mass, from 100 to 500 parts by mass and from 500 to 1000 parts by mass.

The timing of addition of the excipient is not particularly limited, and the excipient is added during the extraction, after removal of the insoluble residues during the production of the extract, before formation into a powder, and the like. The addition is carried out preferably after removal of the insoluble residues or before formation into a powder, and more preferably after removal of the insoluble residues, from the viewpoint of improving the filtration property.

A method of producing the benzyl glucosinolate-containing composition of this embodiment includes a method of producing a benzyl glucosinolate-containing composition including, for example, mixing a *moringa* extract with an excipient, wherein the blending amount of the above excipient is from 65 to 1,000 parts by mass, based on 100 parts by mass of the dry solid content of the above *moringa* extract.

The benzyl glucosinolate-containing composition of this embodiment inhibits the decomposition of a benzyl glucosinolate, and excellent in stability. Accordingly, the benzyl glucosinolate-containing composition of this embodiment richly contains benzyl glucosinolates, and can exhibit useful physiological functions.

The benzyl glucosinolate-containing composition of this embodiment can be blended with various foodstuff. The foodstuff may be, for example, beverages such as refreshing beverages, carbonated beverages, nutritive beverages, fruit beverages, lactic acid beverages, or concentrated stock solutions or powders for preparing these beverages.

In addition, this benzyl glucosinolate-containing composition can be added to a cold confectionery such as ice cream, sherbet, or frappe (kaki kori), or noodles such as buckwheat noodles (soba), wheat noodles (udon), fen-tiao, skin of dumplings stuffed with minced pork, skin of shao-mai, Chinese noodles or instant noodles. Further this benzyl glucosinolate-containing composition can be added to a confectionery such as a candy, a chewing gum, a chocolate, a tablet candy, gummy candy, a snack, a biscuit, a jerry, a custard pudding, a jam, a cream, or a baked confectionery.

Also, the benzyl glucosinolate-containing composition can be added to a marine or livestock processed food such as tubular roll of steamed fish paste, ham, or sausage, or a dairy product such as a processed milk or a fermented milk, or can be added to a fat or oil and a fat or oil processed food such as salad oil, tempura oil, margarine, mayonnaise, shortening, whipped cream, and salad dressing, or to a seasoning such as a sauce or a gravy sauce, or to a soup, a stew, a salad, a ready-made side dish, or a pickle. In addition, the benzyl glucosinolate-containing composition can be added and used in various forms of health and nutritional supplemental foods such as tablets, capsules and drinks, and other quasi-drugs such as oral cavity refreshing agents that are used in the oral cavity such as oral refreshing agent and oral deodorizing agents, dentifrices, and mouthwashes, emollient creams, emollient lotions, or the like.

The blending amount of the benzyl glucosinolate-containing composition of this embodiment is not particularly limited, and the composition can be blended so as to have a concentration of, for example, from 0.01 to 80% by mass of the foodstuff. As such, the content of the benzyl glucosinolate of this embodiment can be from 0.0006 to 40.0% by mass of the foodstuff.

Since the foodstuff of this embodiment contain a benzyl glucosinolate-containing composition that richly contains benzyl glucosinolates as mentioned above, the foodstuff can exhibit useful physiological functions.

EXAMPLES

Examples of the present invention for solving the first aspect will be explained hereinbelow.

Preparation of *Moringa* Extracts—Examples 1-1 to 1-7

*Moringa* seeds were pulverized with a mill to give a pulverized product of seeds. To 100 g of the pulverized product of seeds, 500 g of deionized water (90° C.) was added, and the mixture was stirred for 5 minutes. Thereafter, 1,500 g of deionized water (10° C.) was added to the mixture to adjust the temperature to 35° C., and the mixture was stirred for 2 hours. Thereafter, the mixture was filtered with a filter paper, and the filtrate was concentrated with a rotary evaporator under a reduced pressure. The concentrated solution obtained was dried with a freeze-drier to give 10 g of a *moringa* extract of Example 1-1.

The same procedures as in Example 1-1 were carried out except that dry *moringa* leaves were pulverized with a mill, and the pulverized product of leaves obtained was used, to give 15 g of a *moringa* extract of Example 1-2.

The same procedures as in Example 1-1 were carried out except that *moringa* stems were pulverized with a hammer-mill, and the pulverized product of stem obtained was used, to give 10 g of a *moringa* extract of Example 1-3.

The same procedures as in Example 1-1 were carried out except that *moringa* sheaths were cut into 1 cm or so, freeze-dried, and pulverized with a mill, and the pulverized product of dry sheath obtained was used, to give 10 g of a *moringa* extract of Example 1-4.

One-hundred grams of the pulverized product of *moringa* seeds obtained with a mill was deep-fried with an edible oil heated to 140° C. for 5 minutes, 1,500 g of deionized water (35° C.) was added thereto, and the mixture was stirred for 2 hours. Subsequent processes were carried out in the same manner as Example 1-1, to give 8 g of a *moringa* extract of Example 1-5.

One-hundred grams of the pulverized product of *moringa* seeds obtained with a mill was stir-fried with a steel pan heated to 170° C. for 5 minutes, 1,500 g of deionized water (35° C.) was added thereto, and the mixture was stirred for 2 hours. Subsequent processes were carried out in the same manner as Example 1-1, to give 8 g of a *moringa* extract of Example 1-6.

One-hundred grams of the pulverized product of *moringa* seeds obtained with a mill was steamed with a steamer at 100° C. for 5 minutes, 1,500 g of deionized water (35° C.) was added thereto, and the mixture was stirred for 2 hours. Subsequent processes were carried out in the same manner as Example 1-1, to give 7 g of a *moringa* extract of Example 1-7.

Comparative Examples 1-1, 1-3, 1-5 and 1-7

*Moringa* seeds were pulverized with a mill to give a pulverized product of seeds. To 100 g of the pulverized product of seeds, 2,000 g of deionized water (90° C.) was added, and the mixture was stirred for 2 hours. Thereafter, the mixture was filtered with a filter paper, and the filtrate was concentrated with a rotary evaporator under a reduced pressure. The concentrated solution obtained was dried with a freeze-drier to give 15 g of a *moringa* extract of Comparative Example 1-1.

The same procedures as in Comparative Example 1-1 were carried out except that dry *moringa* leaves were pulverized with a mill, and the pulverized product of leaves obtained was used, to give 20 g of a *moringa* extract of Comparative Example 1-3.

The same procedures as in Comparative Example 1-1 were carried out except that *moringa* stems were pulverized with a hammer-mill, and the pulverized product of stem obtained was used, to give 20 g of a *moringa* extract of Comparative Example 1-5.

The same procedures as in Comparative Example 1-1 were carried out except that *moringa* sheaths were cut into 1 cm or so, freeze-dried, and pulverized with a mill, and the pulverized product of dry sheath obtained was used, to give 18 g of a *moringa* extract of Comparative Example 1-7.

Comparative Examples 1-2, 1-4, 1-6 and 1-8

*Moringa* seeds were pulverized with a mill to give a pulverized product of seeds. To 100 g of the pulverized product of seeds, 2,000 g of 50% (v/v) aqueous ethanol solution (55° C.) was added, and the mixture was stirred for 2 hours. Thereafter, the mixture was filtered with a filter paper, and the filtrate was concentrated with a rotary evaporator under a reduced pressure. The concentrated solution obtained was dried with a freeze-drier to give 12 g of a *moringa* extract of Comparative Example 1-2.

The same procedures as in Comparative Example 1-2 were carried out except that dry *moringa* leaves were pulverized with a mill, and the pulverized product of leaves obtained was used, to give 25 g of a *moringa* extract of Comparative Example 1-4.

The same procedures as in Comparative Example 1-2 were carried out except that *moringa* stems were pulverized with a hammer-mill, and the pulverized product of stem obtained was used, to give 25 g of a *moringa* extract of Comparative Example 1-6.

The same procedures as in Comparative Example 1-2 were carried out except that *moringa* sheaths were cut into 1 cm or so, freeze-dried, and pulverized with a mill, and the pulverized product of dry sheath obtained was used, to give 20 g of a *moringa* extract of Comparative Example 1-8.

Comparative Example 1-9

*Moringa* seeds were pulverized with a mill to give a pulverized product of seeds. To 100 g of the pulverized product of seeds, 2,000 g of deionized water (35° C.) was added, and the mixture was stirred for 2 hours. Thereafter, the mixture was filtered with a filter paper, and the filtrate was concentrated with a rotary evaporator under a reduced pressure. The concentrated solution obtained was dried with a freeze-drier to give 8 g of a *moringa* extract of Comparative Example 1-9.

<Content of Benzyl Glucosinolates>

The content of benzyl glucosinolates (content of BGLs, calculated as dry extract solid content) of the *moringa* extracts of each of Examples and Comparative Examples was analyzed based on the following conditions. The results are shown in Table 1.

An aqueous *moringa* extract solution (concentration: 0.2% w/v) of each of Examples and Comparative Examples was prepared. Myrosinase manufactured by Sigma was added to these sample solutions, and the mixture was reacted at 30° C. for 16 hours. The reaction solution was diluted with a phosphate buffered solution (pH 8.5), 1.2-benzenedithiol was added thereto, the mixture was treated at 65° C. for 2 hours, and a reaction product (1,3-benzenedithiol-2-thione) contained in the treated product was subjected to quantification analysis with a reverse-phase high-performance liquid chromatography under the following conditions:
HPLC: LC-20AD (SHIMADZU Corporation)
Column: L-Column ODS (manufacturer: General Incorporated Foundation, Chemical Evaluation and Research Institute, Japan, inner diameter: 4.6 mm, length: 250 mm, particle size: 5 microns)
Sample injection amount: 10 μL
Detection: UV 365 nm
Solvent: Water/Methanol (20/80, v/v)
Flow rate: 0.5 mL/min <Detection of Alkaloid>

Whether or not an alkaloid is detected from a *moringa* extract of each of Examples and Comparative Examples was analyzed by a thin-layer chromatography. The results are shown in Table 1.

Sample: methanol solutions of Examples and Comparative Examples (concentration: 1 mg/mL)
Amount dropped to plate: 100 μL (amount dropped of sample in the form of solid: about 100 micrograms)
Thin-layer plate: Silica Gel 60F manufactured by Merck
Developing solvent: Chloroform/methanol/25% aqueous ammonium (75/25/2, v/v/v)
Coloring reagent: Dragendorff reagent <DPPH Radical Scavenging Activity>

In order to confirm the usefulness of the *moringa* extract of each of Examples and Comparative Examples, a DPPH radical scavenging activity was analyzed with respect to a method by Rao et al. (Reference: *Austin J Nutr Metab*—Volume 1, Issue 1-2014).

Specifically, 100 mg of each sample (dry powder) was dissolved in 100 ml of deionized water, and gradually diluted to adjust to a concentration of 0.5, 0.25, 0.125 and 0.6125 mg/ml. To 0.05 ml of sample solutions having each concentration, 1 ml of 2,2-diphenyl-1-picrylhydrazil (DPPH) solution in ethanol (concentration: 0.1 mM) and 0.45 ml of 50 mM Tris-HCl buffer (pH 7.4) were added, the mixture was kept in a dark place at an ambient temperature for 1 hour, and thereafter absorbance was measured at 517 nm to calculate 50% inhibitory concentration (IC50).

*Moringa* extracts of Examples 1-1 to 1-7 had high contents of benzyl glucosinolates, and an excellent DPPH radical scavenging activity, and were confirmed to have anti-oxidation action.

On the other hand, *moringa* extracts of Comparative Examples 1-1 to 1-9 which were subjected to hot water extraction at 90° C. for 2 hours or ethanol extraction at 55° C. for 2 hours had lower contents of benzyl glucosinolates than those of Examples 1-1 to 1-7, and were not found to have DPPH radical scavenging activity.

In addition, an alkaloid was not detected from all of *moringa* extracts of Examples 1-1 to 1-7, so that these extracts had no problems in safety as shown in the following safety evaluations 1 and 2.

<Safety Evaluation 1>

A single dose test (rat) was carried out in order to simply evaluate the safety of the obtained *moringa* extract of Example 1-1. As a result, no rats died even when 5 g and 2.5 g of the extract were ingested per kg of body weight. Accordingly, it is thought that there is no safety problem in the *moringa* extract of Example 1-1.

<Safety Evaluation 2>

Using the obtained extract powders of Example 1-1 and Comparative Example 1-3, an abortion activity was confirmed in an animal experiment using rats for the safety of the extracts. Specifically, female albino rats of 8 to 10 week-old (a body weight range from 160 to 200 g per rat) were trained under a breeding environment for a given period of time and thereafter paired with male rats. Rats in which sperms have been confirmed by an intravaginal observation after pairing were transferred to other cages, and

TABLE 1

| | Content of BGLs (% w/w), Calculated on Dry Basis | Alkaloid | DPPH Radical Scavenging Activity (IC50, μg/ml) | Total Free Amino Acid Amount (mg/100 g) | Arginine (mg/100 g) |
|---|---|---|---|---|---|
| Ex. 1-1 | 16.3 | Not Detected | 84.2 ± 10.3 | 760 | 259 |
| Ex. 1-2 | 8.2 | Not Detected | 63.0 ± 15.8 | 1,080 | 302 |
| Ex. 1-3 | 6.3 | Not Detected | 269.4 ± 30.3 | 420 | 84 |
| Ex. 1-4 | 7.8 | Not Detected | 530.8 ± 25.9 | 230 | 20 |
| Ex. 1-5 | 15.2 | Not Detected | 76.3 ± 8.8 | 610 | 165 |
| Ex. 1-6 | 13.8 | Not Detected | 91.2 ± 7.2 | 420 | 137 |
| Ex. 1-7 | 15.8 | Not Detected | 88.4 ± 6.1 | 950 | 307 |
| Comp. Ex. 1-1 | 5.2 | Not Detected | >1,000 | 987 | 341 |
| Comp. Ex. 1-2 | 1.2 | Not Detected | >1,000 | (Not Analyzed) | (Not Analyzed) |
| Comp. Ex. 1-3 | 2.5 | Detected | >1,000 | 158 | 12 |
| Comp. Ex. 1-4 | 0.3 | Detected | >1,000 | (Not Analyzed) | (Not Analyzed) |
| Comp. Ex. 1-5 | 2.3 | Detected | >1,000 | (Not Analyzed) | (Not Analyzed) |
| Comp. Ex. 1-6 | 0.5 | Detected | >1,000 | (Not Analyzed) | (Not Analyzed) |
| Comp Ex. 1-7 | 3.6 | Detected | >1,000 | (Not Analyzed) | (Not Analyzed) |
| Comp. Ex. 1-8 | Not Detected | Detected | >1,000 | (Not Analyzed) | (Not Analyzed) |
| Comp. Ex. 1-9 | 4.3 | Not Detected | >1,000 | 563 | 186 | the rats were subjected to the forced administration with Example 1-1 and Comparative Example 1-3 at a dose of 200 mg per day, per kg of body weight for 10 days to confirm the conditions of intrauterine embryos after administration. As a control, a test group which was allowed to eat food and water ad libitum after pairing was set. For each test group, 7 rats were used. As a result, in rats which were ingested with Comparative Example 1-3, all intrauterine embryos were dead, even though the pairing has been confirmed. However, in the group ingested with Example 1-1 and the control group, intrauterine embryos exhibited similar development. Accordingly, it is thought that there no safety problems in the *moringa* extract of Example 1-1.

Formulation Example 1-1: Refreshing Beverage

| (Composition) | (parts by mass) |
| --- | --- |
| Moringa Extract of Example 1-1 | 0.5 |
| Fructose Glucose Syrup | 11.0 |
| Citric Acid | 0.2 |
| Trisodium Citrate | 0.06 |
| L-Ascorbic Acid | 0.01 |
| Flavor | 0.2 |
| Pigment | 0.1 |
| Water | 87.93 |
| Total Amount | 100.00 |

Formulation Example 1-2: Carbonated Beverage

| (Composition) | (parts by mass) |
| --- | --- |
| Moringa Extract of Example 1-1 | 0.5 |
| Granulated Sugar | 8.0 |
| Concentrated Lemon Juice | 1.0 |
| L-Ascorbic Acid | 0.01 |
| Citric Acid | 0.10 |
| Sodium Citrate | 0.04 |
| Coloring Agent | 0.05 |
| Flavor | 0.15 |
| Carbonated Water | 90.15 |
| Total Amount | 100.00 |

Formulation Example 1-3: Candy

| (Composition) | (parts by mass) |
| --- | --- |
| Moringa Extract of Example 1-1 | 0.5 |
| Sugar | 47.0 |
| Glucose Syrup | 49.0 |
| Flavor | 1.0 |
| Water | 2.0 |
| Total Amount | 100.00 |

Formulation Example 1-4: Troche

| (Composition) | (parts by mass) |
| --- | --- |
| Moringa Extract of Example 1-1 | 0.5 |
| Gum Arabic | 6.0 |
| Glucose | 72.0 |
| Dipotassium Hydrogenphosphate | 0.2 |
| Potassium Dihydrogenphosphate | 0.1 |
| Lactose | 17.0 |
| Flavor | 0.1 |
| Magnesium Stearate | 4.1 |
| Total Amount | 100.00 |

Formulation Example 1-5: Tablet

| (Composition) | (parts by mass) |
| --- | --- |
| Moringa Extract of Example 1-1 | 80.0 |
| Crystalline Cellulose | 10.0 |
| Reduced Maltose Glucose Syrup | 6.0 |
| Calcium Stearate | 2.0 |
| Shellac | 2.0 |
| Total Amount | 100.00 |

Formulation Example 1-6: Powdered Refreshing Beverage

| (Composition) | (parts by mass) |
| --- | --- |
| Moringa Extract of Example 1-1 | 5.0 |
| Dextrin | 65.0 |
| Raspberry Juice Powder | 15.0 |
| Black Tea Extract Powder | 5.0 |
| Oligosaccharide | 5.0 |
| Cyclic Oligosaccharide | 2.5 |
| Flavor | 0.9 |
| Citric Acid | 1.0 |
| Trisodium Citrate | 0.3 |
| Stevia Extract | 0.3 |
| Total Amount | 100.00 |

Formulation Example 1-7: Gummy Candy

| (Composition) | (parts by mass) |
| --- | --- |
| Moringa Extract of Example 1-1 | 10.0 |
| Sugar | 30.0 |
| Glucose Syrup | 32.0 |
| Reduced Glucose Syrup | 12.0 |
| Gum Arabic | 5.0 |
| Ion Exchanged Water | 5.0 |
| Gelatin | 5.0 |
| Coloring Agent | 0.2 |
| Flavor | 0.8 |
| Total Amount | 100.00 |

Formulation Example 1-8: Chewing Gum

| (Composition) | (parts by mass) |
|---|---|
| Moringa Extract of Example 1-1 | 0.05 |
| Gum Base | 20.0 |
| Calcium Carbonate | 2.0 |
| Stevia Extract | 0.1 |
| Lactose | 76.85 |
| Flavor | 1.0 |
| Total Amount | 100.00 |

Formulation Example 1-9: Caramel

| (Composition) | (parts by mass) |
|---|---|
| Moringa Extract of Example 1-1 | 5.0 |
| Granulated Sugar | 27.0 |
| Glucose Syrup | 20.0 |
| Powdered Milk | 40.0 |
| Hydrogenated Oil | 4.0 |
| Salt | 0.6 |
| Flavor | 0.2 |
| Water | 3.2 |
| Total Amount | 100.00 |

Formulation Example 1-10: Jerry (Coffee Jerry)

| (Composition) | (parts by mass) |
|---|---|
| Moringa Extract of Example 1-1 | 1.0 |
| Granulated Sugar | 15.0 |
| Gelatin | 1.0 |
| Coffee Extract | 5.0 |
| Water | 78.0 |
| Total Amount | 100.00 |

Formulation Example 1-11: Ice Cream

| (Composition) | (parts by mass) |
|---|---|
| Moringa Extract of Example 1-1 | 1.0 |
| Heavy Cream (45% Fat) | 33.8 |
| Powdered Nonfat Milk | 11.0 |
| Granulated Sugar | 14.8 |
| Sweetened Egg Yolk | 0.3 |
| Vanilla Essence | 0.1 |
| Water | 39.0 |
| Total Amount | 100.00 |

Formulation Example 1-12: Custard Pudding

| (Composition) | (parts by mass) |
|---|---|
| Moringa Extract of Example 1-1 | 0.1 |
| Milk | 47.5 |
| Whole Egg | 31.9 |
| White Soft Sugar | 17.1 |
| Water | 3.4 |
| Total Amount | 100.00 |

Formulation Example 1-13: Dentifrice

| (Composition) | (parts by mass) |
|---|---|
| Moringa Extract of Example 1-1 | 0.05 |
| Calcium Hydrogendiphosphate | 42.0 |
| Glycerol | 18.0 |
| Carrageenan | 0.9 |
| Sodium Lauryl Sulfate | 1.2 |
| Sodium Saccharin | 0.09 |
| Butyl Paraoxybenzoate | 0.005 |
| Flavor | 1.0 |
| Water | 36.755 |
| Total Amount | 100.00 |

Formulation Example 1-14: Mouthwash

| (Composition) | (parts by mass) |
|---|---|
| Moringa Extract of Example 1-1 | 0.05 |
| Sodium Lauryl Sulfate | 0.8 |
| Glycerol | 7.0 |
| Sorbitol | 5.0 |
| Ethyl Alcohol | 15.0 |
| l-Menthol | 0.05 |
| Flavor | 0.04 |
| Sodium Saccharin | 0.1 |
| Water | 71.96 |
| Total Amount | 100.00 |

Formulation Example 1-15: Emollient Cream

| (Composition) | (parts by mass) |
|---|---|
| Moringa Extract of Example 1-1 | 0.1 |
| Beeswax | 2.0 |
| Stearyl Alcohol | 5.0 |
| Stearic Acid | 8.0 |
| Squalane | 10.0 |
| Self-Emulsifiable Propylene Glycol Monostearate | 3.0 |
| Polyoxyethylene Cetyl Ether (20EO) | 1.0 |
| Flavor | 0.5 |
| Antioxidant | trace |
| Preservative | trace |
| Propylene Glycol | 4.8 |
| Glycerol | 3.0 |
| Sodium Hyaluronate | 0.1 |
| Triethanolamine | 1.0 |
| Purified Water | 61.5 |
| Total Amount | 100.00 |

Formulation Example 1-16: Emollient Lotion

| (Composition) | (parts by mass) |
|---|---|
| Moringa Extract of Example 1-1 | 0.1 |
| Stearic Acid | 2.0 |
| Cetanol | 1.5 |
| Vaseline | 3.0 |
| Lanolin Alcohol | 2.0 |
| Liquid Paraffin | 10.0 |
| Polyoxyethylene Monooleate (10EO) | 2.0 |
| Flavor | 0.5 |
| Antioxidant | trace |
| Preservative | trace |
| Propylene Glycol | 4.8 |
| Glycerol | 3.0 |
| Sodium Hyaluronate | 0.1 |
| Triethanolamine | 1.0 |
| Purified Water | 70.0 |
| Total Amount | 100.00 |

Examples of the present invention for solving the second aspect will be explained hereinbelow.

Preparation of PPAR Activator

*Moringa* seeds were pulverized with a mill to give a pulverized product of seeds. To 100 g of the pulverized product of seeds, 500 g of deionized water (90° C.) was added, and the mixture was stirred for 5 minutes. Thereafter, 1,500 g of deionized water (10° C.) was added thereto to adjust the temperature to 35° C., and the extract was extracted while stirring for 2 hours. The extract was then filtered with a filter paper, and the filtrate was concentrated with a rotary evaporator under a reduced pressure. The concentrated solution obtained was dried with a freeze-drier to give 10 g of a seed extract. The seed extract obtained was used as a PPAR activator. Whether or not an alkaloid was detected from the PPAR activator was analyzed with a thin-layer chromatography (under the following conditions). As a result, no colored spots were found, and an alkaloid was not detected.

Sample: Methanol solution of a PPAR activator (concentration: 1 mg/mL)
Amount dropped to plate: 100 μL (amount dropped of sample in the form of solid: about 100 micrograms)
Thin-layer plate: Silica Gel 60F manufactured by Merck
Developing solvent: Chloroform/methanol/25% aqueous ammonia (75/25/2, v/v/v)
Coloring reagent: Dragendorff reagent Test Examples Examples 2-1 and 2-2

BAECs (bovine arterial endothelial cells) were inoculated in a culture plate, and the cells were cultured overnight (15 hours) under the conditions of 37° C. at 5% $CO_2$. DMEM (High Glucose) (nacalai tesque) supplemented with 10% of Fetal Bovine Serum (SIGMA) was used as a medium. Next, TransIT-LT1 (Mirus) was used to co-transduce a reporter vector with a PPAR responsible element (PPRE) (tK-PPREx3-LUC), expression vectors of human PPARα, β/δ and γ (respectively, GS-hPPARα, pCMX-hNUCI and pCMX-hPPARg1), and a β-galactosidase expression vector (pSV-β-Galactosidase) into the cells, and the cells were cultured for 4 hours under the conditions of 37° C. at 5% $CO_2$. After exchanging the medium, the cells were cultured for additional 24 hours. After cultivation, aqueous solutions of PPAR activators prepared as mentioned above (Example 2-1: 0.004% by mass, and Example 2-2: 0.006% by mass) were added to each well in an amount of 25 μl, and the wells were cultured for 24 hours. Incidentally, cells to which only 25 μl of distilled water was added were cultured and used as a control group. After termination of cultivation, cells were harvested and luciferase activity of a cell extract was measured using Luciferase Assay Reagent (Progma). Here, the gene introduction efficiency was compensated with an enzymatic activity of β-galactosidase. For each Example, the ratio of average (n=3) of light emission intensity of Examples and the control group (Examples/control group) was calculated to define a relative luciferase activity to the control group as the PPAR activation ability of Examples. These results are shown in a graph of FIG. 1.

As can be seen from FIG. 1, it was found that each of PPARs was activated by adding PPAR activators containing *moringa* seeds extracts, particularly activation of PPARβ/δ involving in lipid metabolism of a skeletal muscle and PPARγ involving in differentiation induction of a fat cell or lipogenesis were remarkable.

Preparation of Tablet

A tablet with the PPAR activator prepared as mentioned above was prepared with a composition listed in Table 2-1, to make a tablet of Example 2-3. In addition, a tablet without containing a PPAR activator was together prepared, to make a tablet of Comparative Example 2-1. A volunteer test using these tablets was carried out as follows.

Volunteer Test

Volunteer Subject

Volunteer subjects were defined as 8 male office workers of ages from 35 to 55 years, mainly involved with desk work, and not performing a daily exercise (without ingesting other drugs or supplements, without going to a hospital for treatment, and taking regulated dietary life).

Ingestion Method

The test was carried out as double blind comparison test. Specifically, the volunteers ingested any one of tablets of Example 2-3 and Comparative Example 2-1 at a dose of 2 tablets per day for 4 weeks continuously, in a state that the volunteers could not understand which tablets were ingested. After ingestion, the volunteers have spent the time period of wash out for one month, and then ingested with tablets which are different from previously ingested tablets at a dose of 2 per day for 4 weeks continuously.

Evaluation Method

The evaluation method was carried out as follows.
1. Systemic fatigue feeling: The volunteers themselves objectively evaluated any changes before the ingestion and after 4-week ingestion, and marked those with effective changes as ○ or no changes or worsened ones as x. The number of the volunteers who marked ○ was listed in Table 2-2 (at the time of ingestion of Example 2-3) and Table 2-3 (at the time of ingestion of Comparative Example 2-1).
2. Asthenopic fatigue feeling: Evaluation was carried out in the same manner as the systemic fatigued feeling.
3. Ambulation distance for 3 minutes: Evaluation was carried out as an index of a systemic endurance. Specifically, it was measured how many meters the volunteers walked in 3 minutes, using a 400 m track in a track and field stadium. The differences between the distance after 4-week ingestion and the distance before the ingestion were expressed as an increase or decrease, and the volunteers in which distance was lengthened were listed as a person showing effects in Table 2-2 (at the time of ingestion of Example 2-3) and Table 2-3 (at the time of ingestion of Comparative Example 2-1).
4. Increase or decrease of maximum blood pressure: The blood pressures after 4-week ingestion and before the ingestion were measured, the differences were expressed as an increase or decrease, and the volunteers in which numbers decreased (minus) were listed as a person showing effects in Table 2-2 (at the time of ingestion of Example 2-3) and Table 2-3 (at the time of ingestion of Comparative Example 2-1).
5. Increase or decrease of neutral lipid in blood: The neutral lipids in blood after 4-week ingestion and before the ingestion were measured, the differences were expressed as an increase or decrease, and the volunteers in which numbers decreased (minus) were listed as a person showing effects in Table 2-2 (at the time of ingestion of Example 2-3) and Table 2-3 (at the time of ingestion of Comparative Example 2-1).

TABLE 2-1

| (Composition) | Example 2-3 | | Comparative Example 2-1 | |
|---|---|---|---|---|
| | (parts by mass) | Formulation Amount Per Tablet, (mg) | (parts by mass) | Formulation Amount Per Tablet, (mg) |
| PPAR Activator | 80.0 | 160 | | |
| Crystalline Cellulose | 10.0 | 20 | 10.0 | 20 |
| Reduced Maltose Glucose Syrup Powder | 6.0 | 12 | 86.0 | 172 |
| Calcium Stearate | 2.0 | 4 | 2.0 | 4 |
| Shellac | 2.0 | 4 | 2.0 | 4 |
| Total Amount | 100.0 | 200 | 100.0 | 200 |

TABLE 2-2

Ingested Tablet: Example 2-3

| Volunteer Name | Systemic Fatigue Feeling | Asthenopic Fatigue Feeling | Increase or Decrease of Ambulation Distance for 3 min (m) | Increase or Decrease of Maximum Blood Pressure (mmHg) | Increase or Decrease of Neutral Lipid in Blood (mg/dl) | Number of Items in Which Effects Were Found |
|---|---|---|---|---|---|---|
| A | ○ | ○ | 22 | −8 | −25 | 5 |
| B | ○ | X | 15 | 10 | −20 | 3 |
| C | X | ○ | −16 | −15 | 30 | 2 |
| D | ○ | X | −20 | 15 | −15 | 2 |
| E | ○ | ○ | 30 | −10 | −17 | 5 |
| F | ○ | ○ | 26 | 8 | −23 | 4 |
| G | X | ○ | 14 | −12 | −13 | 4 |
| H | ○ | X | 9 | −13 | 29 | 3 |
| Persons with Effects (out of 8) | 6 | 5 | 6 | 5 | 6 | |

TABLE 2-3

Ingested Tablet: Comparative Example 2-1

| Volunteer Name | Systemic Fatigue Feeling | Asthenopic Fatigue Feeling | Increase or Decrease of Ambulation Distance for 3 min (m) | Increase or Decrease of Maximum Blood Pressure (mmHg) | Increase or Decrease of Neutral Lipid in Blood (mg/dl) | Number of Items in Which Effects Were Found |
|---|---|---|---|---|---|---|
| A | X | X | −18 | 5 | −3 | 1 |
| B | ○ | X | 5 | 9 | 5 | 2 |
| C | X | ○ | −26 | 4 | 29 | 1 |
| D | X | X | −20 | 6 | 36 | 0 |
| E | X | X | −23 | 9 | −17 | 1 |
| F | X | ○ | −14 | 12 | −10 | 2 |
| G | X | X | 10 | 13 | 16 | 1 |
| H | X | X | −8 | −11 | 38 | 1 |
| Person with Effects (out of 8) | 1 | 2 | 2 | 1 | 3 | |

Table 2-2 (the results of ingestion of Example 2-3) showed markedly improving tendency in all of items as compared to Table 2-3 (the results of ingestion of Comparative Example 2-1). When ingesting Example 2-3, it was confirmed that all of 8 volunteers showed improving effects in two or more items, but, markedly improving effects were not found when ingesting Comparative Example 2-1. Incidentally, all volunteers everyday ingested two tablets per day for 4 weeks in accordance with the instructions, and no abnormality in physical conditions by ingesting tablets were found in all volunteers.

Formulation Example 2-1: Refreshing Beverage

| (Composition) | (parts by mass) |
|---|---|
| PPAR Activator of Example 2-1 | 0.5 |
| Fructose Glucose Syrup | 11.0 |
| Citric Acid | 0.2 |
| Trisodium Citrate | 0.06 |
| L-Ascorbic Acid | 0.01 |
| Flavor | 0.2 |
| Pigment | 0.1 |
| Water | 87.93 |
| Total Amount | 100.00 |

Formulation Example 2-2: Candy

| (Composition) | (parts by mass) |
|---|---|
| PPAR Activator of Example 2-1 | 1.0 |
| Sugar | 47.0 |
| Glucose Syrup | 49.0 |
| Flavor | 1.0 |
| Water | 2.0 |
| Total Amount | 100.00 |

Formulation Example 2-3: Gummy Candy

| (Composition) | (parts by mass) |
|---|---|
| PPAR Activator of Example 2-1 | 10.0 |
| Sugar | 30.0 |
| Glucose Syrup | 32.0 |
| Reduced Glucose Syrup | 12.0 |
| Gum Arabic | 5.0 |
| Ion Exchanged Water | 5.0 |
| Gelatin | 5.0 |
| Coloring Agent | 0.2 |
| Flavor | 0.8 |
| Total Amount | 100.00 |

Formulation Example 2-4: Chocolate

| (Composition) | (parts by mass) |
|---|---|
| PPAR Activator of Example 2-1 | 1.0 |
| Sugar | 44.5 |
| Whole Powdered Milk | 20.0 |
| Cocoa Butter | 20.0 |
| Cocoa Mass | 13.5 |
| Emulsifier | 0.5 |
| Flavor | 0.5 |
| Total Amount | 100.00 |

Examples of the present invention for solving the third aspect will be explained hereinbelow.

Preparation of Benzyl Glucosinolate-Containing Compositions, Examples 3-1 to 3-5 and Comparative Examples 3-1 to 3-2

*Moringa* seeds were pulverized with a mill to give a pulverized product of seeds. To 100 g of the pulverized product of seeds, 500 g of deionized water (90° C.) was added, and the mixture was stirred for 5 minutes. Thereafter, 1,500 g of deionized water (10° C.) was added thereto to adjust the temperature to 35° C., and the mixture was stirred for 2 hours. The mixture was then filtered with a filter paper, the solid content was measured as a heated residue, maltodextrin in the same amount to the total content of the solid content was added thereto. The dextrin-mixed filtrate was concentrated with a rotary evaporator under a reduced pressure, and the concentrated solution obtained was dried with a freeze-drier to give 20 g of a benzyl glucosinolate-containing composition of Example 3-1.

The same procedures as in Example 3-1 were carried out except that cyclodextrin was used in place of maltodextrin, to give 20 g of a benzyl glucosinolate-containing composition of Example 3-2.

The same procedures as in Example 3-1 were carried out except that galactomannan was used in place of maltodextrin, to give 20 g of a benzyl glucosinolate-containing composition of Example 3-3.

The same procedures as in Example 3-1 were carried out except that the amount of maltodextrin added was changed to 75 parts by mass based on 100 parts by mass of the total content of *moringa* extract solid content, to give 16 g of a benzyl glucosinolate-containing composition of Example 3-4.

The same procedures as in Example 3-1 were carried out except that the amount of maltodextrin added was changed to 1,000 parts by mass based on 100 parts by mass of the total content of *moringa* extract solid content, to give 110 g of a benzyl glucosinolate-containing composition of Example 3-5.

The same procedures as in Example 3-1 were carried out except that maltodextrin was not added, and the mixture was concentrated under a reduced pressure after the filtration, to give 10 g of a benzyl glucosinolate-containing composition of Comparative Example 3-1.

The same procedures as in Example 3-1 were carried out except that the amount of maltodextrin added was changed to 50 parts by mass based on 100 parts by mass of the total content of *moringa* extract solid content, to give 13 g of a benzyl glucosinolate-containing composition of Comparative Example 3-2.

<Stability>

The benzyl glucosinolate-containing composition of each of Examples and Comparative Examples was placed into a polyethylene bag (internal bag) and an aluminum bag (external bag), and stored at 55° C. The samples were taken out from the bags at every given time period, and the content of benzyl glucosinolates (content of BGLs) was analyzed based on the following conditions. The analyzing results are shown in Table 3.

An aqueous *moringa* extract solution (concentration: 0.2% w/v) of each of Examples and Comparative Examples was prepared. Myrosinase manufactured by Sigma was added to these sample solutions, and the mixture was reacted at 30° C. for 16 hours. The reaction solution was diluted in a phosphate buffered solution (pH 8.5), 1.2-benzenedithiol was added thereto, the mixture was treated at 65° C. for 2 hours, and the product (1,3-benzenedithiol-2-thione) contained in the treated product was subjected to quantification analysis with a reverse-phase high-performance liquid chromatography under the following conditions:

HPLC: LC-20AD (SHIMADZU Corporation)
Column: L-Column ODS (manufacturer: General Incorporated Foundation, Chemical Evaluation and Research Institute, Japan, inner diameter: 4.6 mm, length: 250 mm, particle size: 5 microns)
Sample injection amount: 10 μL
Detection: UV 365 nm
Solvent: Water/Methanol (20/80, v/v)
Flow rate: 0.5 mL/min

TABLE 3

| Storage Period (Weeks) | Content of BGLs (% w/w), calculated as pure extract | | | | | | |
|---|---|---|---|---|---|---|---|
| | Ex. 3-1 | Ex. 3-2 | Ex. 3-3 | Ex. 3-4 | Ex. 3-5 | Comp. Ex. 3-1 | Comp. Ex. 3-2 |
| 0 | 12.64 | 11.64 | 10.23 | 13.45 | 12.35 | 6.42 | 9.38 |
| 2 | 11.57 | 9.12 | 8.52 | 10.39 | 10.86 | 5.27 | 6.34 |
| 4 | 7.68 | 5.64 | 4.28 | 8.65 | 7.98 | 2.89 | 3.97 |
| 24 | 5.23 | 2.34 | 3.28 | 6.24 | 5.98 | 0.57 | 0.89 |

It could be seen from Examples 3-1 to 3-5 and Comparative Examples 3-1 to 3-2 that the blending of an excipient is preferred for stabilizing benzyl glucosinolate, and that the blending of the excipient in 75 parts by mass or more based on 100 parts by mass of the *moringa* extract on dry solid basis is preferred. In addition, it could be seen that among the excipients, the composition of Example 3-1 containing maltodextrin is more preferred.

Formulation Example 3-1: Refreshing Beverage

| (Composition) | (parts by mass) |
|---|---|
| Composition of Example 3-1 | 1.0 |
| Fructose Glucose Syrup | 10.5 |
| Citric Acid | 0.2 |
| Trisodium Citrate | 0.06 |
| L-Ascorbic Acid | 0.01 |
| Flavor | 0.2 |
| Pigment | 0.1 |
| Water | 87.93 |
| Total Amount | 100.00 |

Formulation Example 3-2: Carbonated Beverage

| (Composition) | (parts by mass) |
|---|---|
| Composition of Example 3-1 | 1.0 |
| Granulated Sugar | 7.5 |
| Concentrated Lemon Juice | 1.0 |
| L-Ascorbic Acid | 0.01 |
| Citric Acid | 0.10 |
| Sodium Citrate | 0.04 |
| Coloring Agent | 0.05 |
| Flavor | 0.15 |
| Carbonated Water | 90.15 |
| Total Amount | 100.00 |

Formulation Example 3-3: Candy

| (Composition) | (parts by mass) |
|---|---|
| Composition of Example 3-1 | 2.0 |
| Sugar | 46.0 |
| Glucose Syrup | 49.0 |
| Flavor | 1.0 |
| Water | 2.0 |
| Total Amount | 100.00 |

Formulation Example 3-4: Troche

| (Composition) | (parts by mass) |
|---|---|
| Composition of Example 3-1 | 1.0 |
| Gum Arabic | 6.0 |
| Glucose | 71.0 |
| Dipotassium Hydrogenphosphate | 0.2 |
| Potassium Dihydrogenphosphate | 0.1 |
| Lactose | 17.0 |
| Flavor | 0.1 |
| Magnesium Stearate | 4.1 |
| Total Amount | 100.00 |

Formulation Example 3-5: Tablet

| (Composition) | (parts by mass) |
|---|---|
| Composition of Example 3-1 | 80.0 |
| Crystalline Cellulose | 10.0 |
| Reduced Maltose Glucose Syrup Powder | 6.0 |
| Calcium Stearate | 2.0 |
| Shellac | 2.0 |
| Total Amount | 100.00 |

Formulation Example 3-6: Powdered Refreshing Beverage

| (Composition) | (parts by mass) |
|---|---|
| Composition of Example 3-1 | 10.0 |
| Dextrin | 60.0 |
| Raspberry Juice Powder | 15.0 |
| Black Tea Extract Powder | 5.0 |
| Oligosaccharide | 5.0 |
| Cyclic Oligosaccharide | 2.5 |
| Flavor | 0.9 |
| Citric Acid | 1.0 |
| Trisodium Citrate | 0.3 |
| Stevia Extract | 0.3 |
| Total Amount | 100.00 |

Formulation Example 3-7: Gummy Candy

| (Composition) | (parts by mass) |
|---|---|
| Composition of Example 3-1 | 20.0 |
| Sugar | 25.0 |
| Glucose Syrup | 27.0 |
| Reduced Glucose Syrup | 12.0 |
| Gum Arabic | 5.0 |
| Ion Exchanged Water | 5.0 |
| Gelatin | 5.0 |
| Coloring Agent | 0.2 |
| Flavor | 0.8 |
| Total Amount | 100.00 |

The present invention is not limited by the embodiments and Examples mentioned above at all. The present invention may take various embodiments within the matter not departing the gist of the present invention.

INDUSTRIAL APPLICABILITY

The *moringa* extract of the present invention for solving the first aspect is useful in the field of foodstuff or the like. In addition, the PPAR activator of the present invention for solving the second aspect has an excellent PPAR activation action, can be ingested for a long term without problems of side effects, and can be preferably used for foodstuff or the like. Accordingly, the PPAR activator of the present invention for solving the second aspect can be expected for the use as a food, a supplement, or a medicament not only for, for example, prevention of disease such as insulin resistance, hyperinsulinism, Type 2 diabetes, hypertension, hyperlipidemia, arterial sclerosis and obesity, but also for fatigue recovery or endurance improvement by improving basal metabolism. In addition, the benzyl glucosinolate-containing composition of the present invention for solving the third aspect is useful in the field of foodstuff or the like.

The invention claimed is:

1. A *moringa* extract comprising a benzyl glucosinolate in a content of 6% by mass or more, calculated as a dry solid content of the extract, wherein the extract does not substantially comprise an alkaloid.

2. The *moringa* extract according to claim 1, wherein an extraction solvent of the extract is water.

3. A benzyl glucosinolate-containing composition comprising a *moringa* extract as defined in claim 1 and an excipient.

4. Foodstuff comprising a *moringa* extract as defined in claim 1, wherein the foodstuff is selected from the group consisting of beverages; concentrated original liquids or powders for preparing these beverages; cold confectioneries; noodles; confectioneries; a marine or livestock processed food; a dairy product; a fat or oil and a fat or oil processed food; a seasoning; a soup, a stew, a salad, a ready-made side dish and a pickle; health and nutritional supplemental foods; supplements; oral cavity refreshing agents; and foodstuff for a pet.

* * * * *